United States Patent [19]

Euvrard et al.

[11] Patent Number: 6,015,292

[45] Date of Patent: Jan. 18, 2000

[54] DENTAL REAMERS AND PROCESS FOR MANUFACTURING SAME

[75] Inventors: Hubert Euvrard, Geneuille; Denis Chevillot, Miserey Salines, both of France

[73] Assignee: Micro-Mega International Manufactures, Besancon, France

[21] Appl. No.: 09/012,464

[22] Filed: Jan. 22, 1998

[30] Foreign Application Priority Data

Jan. 29, 1997 [FR] France .................................. 97 01131

[51] Int. Cl.⁷ ...................................................... A61C 5/02
[52] U.S. Cl. .............................................. 433/102; 451/48
[58] Field of Search ................................... 433/102, 224; 451/48

[56] References Cited

U.S. PATENT DOCUMENTS

| | | | |
|---|---|---|---|
| 4,642,942 | 2/1987 | Guhring | 451/48 |
| 5,353,552 | 10/1994 | Hemmings | 451/48 |
| 5,464,362 | 11/1995 | Heath et al. | 451/48 |

*Primary Examiner*—John J. Wilson
*Attorney, Agent, or Firm*—Weiser and Associates, P.C.

[57] ABSTRACT

Dental reamers are manufactured from a cylindrical metallic blank (e.g., made of a nickel-titanium alloy) that is moved at a feed speed $V_A$ past a rotary grinding wheel whose disk, of variable diameter, determines a linear speed $V_L$ at which material is removed. The feed speed $V_A$ is greater than 91440 cm/min, while the linear speed $V_L$ is less than 7.62 cm/min.

8 Claims, No Drawings

DENTAL REAMERS AND PROCESS FOR MANUFACTURING SAME

BACKGROUND OF THE INVENTION

1. Field of the Invention

The present invention relates to a process for manufacturing dental reamers using nickel-titanium alloy (known by the name NITI).

Description of the Related Art p U.S. Pat. No. 5,464,362, which is incorporated herein by reference, describes a process for manufacturing dental reamers from a cylindrical metallic blank. The metallic blank rod is moved at a feed speed $V_A$ past a rotary grinding wheel whose disk, of variable diameter, determines a linear speed $V_L$ relating to the rate at which material is removed from the rod by the rotary grinding wheel which has a grit size $D_G$. According to the '362 patent, the feed speed $V_A$ is between 7.62 and 20.32 cm/min and the grit size $D_G$ is greater than 200 grit.

SUMMARY OF THE INVENTION

Surprisingly, and in complete contradiction with what is presented as being a state of optimum conditions in the prior art process, it has been shown that opposite operating conditions yield at least equal results. The present invention consequently relates to a process for the manufacture of dental reamers using nickel-titanium alloy, said dental reamers being manufactured from a cylindrical metallic blank which is moved at a feed speed $V_A$ past a rotary grinding wheel whose disk, of variable diameter, determines a linear speed $V_L$ relating to the rate at which material is removed, wherein $V_L$ is greater than 91440 cm/min and $V_A$ is less than 7.62 cm/min.

DETAILED DESCRIPTION

According to the present invention, dental reamers are manufactured from a cylindrical metallic blank, generally composed of at least 40% titanium, although this proportion is not critical. The metallic blank rod is moved at a feed speed $V_A$ past a rotary grinding wheel whose disk, of variable diameter, determines a linear speed $V_L$ relating to the rate at which material is removed from the rod by the rotary grinding wheel. Another important parameter is determined by the grit size $D_G$ of the grinding wheel, which in this case is generally a diamond-tipped grinding wheel.

According to the present invention, dental reamers are manufactured from a cylindrical blank made of a nickel-titanium alloy. The cylindrical metallic blank is moved at a feed speed $V_A$ past a rotary grinding wheel whose disk, of variable diameter, determines a linear speed $V_L$ at which material is removed, wherein the feed speed $V_A$ is greater than 91440 cm/min and the linear speed $V_L$ is less than 7.62 cm/min.

In one embodiment, the particles of the grinding wheel will have a grit size of greater than 46 μ and the grinding wheel will be a diamond-tipped grinding wheel. In a preferred embodiment, the feed speed $V_A$ is approximately 2213 rn/min, while the linear speed $V_L$ is approximately 3.2 cm/min.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A process for manufacturing a dental reamer from a cylindrical blank of a nickel-titanium alloy by moving the cylindrical blank at a feed speed $V_A$ past a rotary grinding wheel whose disk, of variable diameter, has a linear speed $V_L$ relating to the rate at which material is removed, wherein the linear speed $V_L$ is greater than about 91440 cm/min and the feed speed $V_A$ is less than about 7.62 cm/min.

2. The process of claim 1, wherein particles of the grinding wheel have a grit size of greater than 46μ.

3. The process of claim 2, wherein the grinding wheel is a diamond-tipped grinding wheel.

4. The process of claim 3, wherein the linear speed $V_L$ is approximately 2213 m/min and the feed speed $V_A$ is approximately 3.2 cm/min.

5. The process of claim 2, wherein the linear speed $V_L$ is approximately 2213 m/min and the feed speed $V_A$ is approximately 3.2 cm/min.

6. The process of claim 1, wherein the grinding wheel is a diamond-tipped grinding wheel.

7. The process of claim 6, wherein the linear speed $V_L$ is approximately 2213 m/min and the feed speed $V_A$ is approximately 3.2 cm/min.

8. The process of claim 1, wherein the linear speed $V_L$ is approximately 2213 m/min and the feed speed $V_A$ is approximately 3.2 cm/min.

* * * * *